United States Patent
Muzykantov et al.

(10) Patent No.: US 7,157,087 B2
(45) Date of Patent: Jan. 2, 2007

(54) ENHANCEMENT OF INTRACELLULAR DELIVERY AND TISSUE TARGETING OF DRUGS AND GENES

(75) Inventors: Vladimir R. Muzykantov, Warwick, PA (US); Steve M. Albelda, Bala Cynwyd, PA (US)

(73) Assignee: Trustees of the University of Pennsylvania, Philadelphia, PA (US)

( * ) Notice: Subject to any disclaimer, the term of this patent is extended or adjusted under 35 U.S.C. 154(b) by 604 days.

(21) Appl. No.: 10/446,422

(22) Filed: May 28, 2003

(65) Prior Publication Data

US 2003/0206911 A1 Nov. 6, 2003

Related U.S. Application Data

(63) Continuation of application No. 09/623,822, filed as application No. PCT/US99/05279 on Mar. 10, 1999, now abandoned.

(60) Provisional application No. 60/077,375, filed on Mar. 10, 1998.

(51) Int. Cl.
*A61K 39/44* (2006.01)
(52) U.S. Cl. ................ 424/178.1; 530/350; 530/387.1; 530/391.7; 424/134.1; 424/183.1
(58) Field of Classification Search ............. 424/178.1, 424/183.1, 182.1, 193.1, 134.1; 530/388.22, 530/387.1, 391.7, 391.1, 350
See application file for complete search history.

(56) References Cited

OTHER PUBLICATIONS

Muzykantov et al., "Streptavidin facilitates internalization and pulmonary targeting of an anti-endothelial cell antibody(platelet-endothelial cell adhesion molecule 1) :A strategy for vascular immunotargeting of drugs", Proc. Natl. Acad. Sci. USA 1999 96:2379-2384.

Muzykantov et al., "The Functional Effects of Biotinylation of Anti-angiotensin-Converting Enzyme Monoclonal Antibody in Terms of Targeting *in Vivo*", Analytical Biochemistry 1995 226:279-287.

Muzykantov et al., "Endothelial cells internalize monoclonal antibody to angiotensin-converting enzyme", American Journal Physiology 1996; L704-L713 vol. 270 (5pt.1).

Liu et al., "Constitutive and Antibody-induced Internalization of Prostate-specific Membrane Antigen[1]", Cancer Research 1998 58:4055-4060.

Kalofonos et al., "Imaging of Tumor in Patients with Indium-111-Labeled Biotin and Streptavidin-Conjugated Antibodies:Preliminary Communication", Journal of Nuclear Medicine 1990 11:1791-1796.

Rosebrough S.F., "Two-step immunological approaches for imaging and therapy", Quarterly Journal Nuclear Med. 1996 40:234-251 XP-002086486.

*Primary Examiner*—Stephen L. Rawlings
(74) *Attorney, Agent, or Firm*—Licata & Tyrrell P.C.

(57) ABSTRACT

A method for enhancing intracellular delivery of effector molecules is provided. The method involves modifying selected antibodies with biotin and streptavidin, conjugating these antibodies with an effector molecule, and delivering the conjugated effector to an intracellular target specifically recognized by the antibody.

3 Claims, No Drawings

ENHANCEMENT OF INTRACELLULAR DELIVERY AND TISSUE TARGETING OF DRUGS AND GENES

INTRODUCTION

This application is a continuation of U.S. application Ser. No. 09/623,822 filed Oct. 25, 2000, now abandoned, which is the U.S. National Stage of PCT Application Ser. No. PCT/US99/05279 filed Mar. 10, 1999, which claims the benefit of priority from U.S. Provisional Application Ser. No. 60/077,375 filed Mar. 10, 1998 each of which are herein incorporated by reference in their entirety.

BACKGROUND OF THE INVENTION

Targeting of drugs or genetic material to defined cells, tissues or organs increases the specificity and effectiveness of drug therapy and reduces the incidence of potentially harmful side effects. Intracellular delivery and proper intracellular processing are required for specific and effective therapeutic applications of certain classes of drugs including, but not limited to, immunotoxins, antioxidants, NO-donors, antibiotics, antisense oligonucleotides, nucleic acids and intracellular hormones. Further, intracellular delivery of gene therapy products is crucial to successful treatment.

In the case of antioxidants, immunotoxins, antisense agents, hormones, gene therapy agents and other therapeutic compounds, referred to herein as "effectors", only limited spontaneous cellular internalization typically occurs. Accordingly, strategies to facilitate or enhance internalization have been developed and include chemical modification with polyethylene glycol (Abuchowski et al. *J. Biol. Chem.* 1977 252(11):3852–3586; Abuchowski et al. *J. Biol. Chem.* 1992 252(11):3578–3581; Beckman et al. *J. Biol. Chem.* 1988 263:6884–6892), encapsulation in liposomes (Freeman et al. *J. Biol. Chem.* 1983 258:12534–12542; Briscoe et al. *Am. J. Physiol.* 1995 12(3):L374–L380), and conjugation with ligands of internalizable receptors (Wagner et al. *Adv. Drug. Del. Rev.* 1994 14:113–135; Chen et al. *FEBS Lett.* 1994 338:167–169).

Although these strategies may facilitate internalization, their applicability is restricted. For example, none of these methods provides targeting of an effector to a specific cell, tissue, or organ, restricting the specificity and safety of the therapeutic agent. Further, these methods utilize cellular mechanisms of internalization leading to accumulation of an effector in the lysosomes and ultimately resulting in degradation and inactivation of the effector compound.

Antibodies recognizing cell-specific surface determinants are useful for targeting compounds to defined cells, tissues, or organs. Chemical conjugation of a cell-specific antibody with an effector has been investigated as a means to achieve specific targeting (Poznansky M. and Juliano, R. *Pharmacol. Rev.* 1984 4:278–345). Antibodies capable of effective internalization can provide intracellular delivery of a drug (Raso, V. *Anal. Biochem.* 1994 222:297–304; Chen et al. *FEBS Lett.* 1994 338:167–169). For example, studies have been performed targeting drugs conjugated with internalizable antibodies against receptors for transferrin, growth factor and folate (Wagner et al. *Adv. Drug. Del. Rev.* 1994 14:113–135; Chen et al. *FEBS Lett.* 1994 338:167–169). Internalizable antibodies, however, underwent massive intracellular degradation in lysosomes (Brisson et al. *Throm. Haremost.* 1992 68:737–743; Raso, V. *Anal. Biochem.* 1994 222:297–304; Reilly et al. *Clin. Pharmacokinet.* 1995 28:126–142; Muzykantov et al. *Circulation* 1997 8:43–44). Accumulation of these antibodies or antibody-conjugated effectors in lysosomes and subsequent lysosomal degradation restrict the applicability of the internalizable antibody as a carrier for intracellular delivery of drugs.

Other potentially useful antibodies that recognize specific antigens abundant on the surface of target cells are "poorly internalizable" (Matzku et al. *Int. J. Cancer* 1988 2:11–14; Reilly et al. *Clin. Pharmacokinet.* 1995 28:126–142). The lack of internalization diminishes intracellular delivery and accumulation in target organs or tissues (Matzku et al. *Int. J. Cancer* 1988 2:11–14; Reilly et al. *Clin. Pharmacokinet.* 1995 28:126–142). Therefore, these "poorly internalizable" antibodies are not useful for intracellular targeting.

Among potential target cells, pulmonary vascular endothelium represents an important target for intracellular delivery of drugs, genes, enzymes, NO-donors and other effectors (Erzurum et al. *Nucl. Acid Res.* 1993 21:1607–1612; von der Leyen et al. *Proc. Natl Acad. Sci. USA* 1995 92:1137–1141; Gibbons, G. and Dzau, V. *Science* 1996 272:689–693; Rodman et al. *Am. J. Respir. Mol. Cell. Biol.* 1997 16:640–649). Several monoclonal antibodies have been studied as potential carriers for intracellular delivery of drugs to endothelial cells. For example, internalizable antibodies against thrombomodulin (Kennel et al. *Nucl. Med. Biol.* 1990 17:193–200; Maruyama et al. *Proc. Natl. Acad. Sci. USA* 1990 87:5744–5748) and E-selectin (Kuijpers et al. *J. Immunol.* 1994 152:5060–69; Spragg et al. *Proc. Natl Acad. Sci. USA* 1997 94:8795–8800) have both been conjugated to drugs for targeting to endothelial cells. However, these internalizable antibodies underwent massive intracellular degradation in lysosomes.

Another example of an antibody carrier that has been tested as a means of internalizing effectors is antibody to angiotensin-converting enzyme (anti-ACE; Muzykantov, V. et al. *Am. Rev. Res. Dis.* 1989 136:1464–1473). The methods utilized were based on the conjugation of an effector with anti-ACE, an antibody that recognizes pulmonary endothelial surface antigen (Danilov et al. *Lab. Invest.* 1991 64:118–124). The anti-ACE carrier provided intracellular targeting (50–60% internalization) and underwent moderate destruction in the lysosomes (15–20% degradation) (Muzykantov et al. *Proc. Natl Acad. Sci. USA* 1996 93:5213–5218). However, the total amount of anti-ACE binding sites in pulmonary endothelium was limited to $2 \times 10^5$ per cell (Muzykantov et al. *Am. J. Physiol.* 1996 270:L704–713). The limited number of binding sites, as well as significant intracellular degradation, limit the utility of this antibody system for intracellular targeting. In addition, anti-ACE accumulation in the lung causes suppression of ACE activity in the tissue (Danilov et al. *Intern. Immunol.* 1994 6:1153–1160). In pathological conditions associated with acute hypotonia, inhibition of ACE activity may lead to dangerous side effects, such as vascular collapse.

Since streptavidin-biotin cross-linker was utilized for conjugation of drugs to anti-ACE, the effects of biotinylation and conjugation with streptavidin on anti-ACE targeting, binding and internalization by endothelium was examined (Muzykantov et al. *Anal. Biochem.* 1995 226:279–287). These studies showed no significant effect of biotinylation and subsequent conjugation with streptavidin on these parameters.

Accordingly, there is a need for antibody systems which provide intracellular targeting of selected cells with a large amount of effector while escaping the lysosomal degradation pathway.

In the present invention, a method is provided for facilitating intracellular delivery to endothelium of a carrier antibody and antibody-conjugated effectors to pulmonary endothelial cells. Further, this methods has been successfully used in other cell types with several antibodies thus demonstrating that applicability of this strategy is not limited to endothelial cells or specific antibodies. The method of the present invention overcomes problems of poor internalization and intracellular degradation in lysosomes, while allowing use of antibodies with higher numbers of binding sites per cell.

SUMMARY OF THE INVENTION

An object of the present invention is to provide a method for enhancing cellular internalization of selected antibodies which comprises biotinylation of a selected antibody followed by conjugation of the biotinylated antibody with streptavidin. The modification of the antibody with streptavidin leads to an increase in the amount of antibody internalized.

Another object of the present invention is to provide a method for enhancing intracellular delivery of an effector to a selected target cell by conjugating the effector with a biotinylated, streptavidin-conjugated antibody that is targeted to the selected cell.

Another object of the present invention is to provide a method for enhancing accumulation of an antibody in a selected tissue by conjugating a biotinylated antibody with streptavidin. The modification of the antibody with streptavidin leads to an increase in the amount of antibody accumulated in the target tissue.

Another object of the present invention is to provide a method for enhancing accumulation of an effector in a selected tissue by conjugating the effector with a biotinylated, streptavidin-conjugated antibody that accumulates in the selected tissue.

Another object of the present invention is to provide a method for selectively killing cells in a selected tissue by administering an effector capable of producing oxidative injury in selected cells of the selected tissue. The effector-antibody conjugate is delivered to selected cells of the selected tissue, and internalization is enhanced by conjugating the effector with a biotinylated, streptavidin-conjugated antibody.

DETAILED DESCRIPTION OF THE INVENTION

Streptavidin (SA) is a tetrameric protein possessing four high affinity binding sites for biotin. Chemical derivatives of biotin developed during the last two decades allow covalent coupling of biotin residues to biomolecules (amino groups, proteins, sugars, lipids, nucleic acids, peptides, etc.) without loss of their specific biological activity. SA crosslinks biotinylated molecules and is widely used as a crosslinking agent (Wilchek, M. and Bayer, E. *Anal. Biochem.* 1988 171:1–32). SA is non-toxic and induces no harmful side effects in animals and human patients (Hnatowich et al. *J. Nucl. Med.* 1987 28:1294–1302; Schecter et al. *Int. J. Cancer* 1991 48:167–172; Rosebrough, S. F. and Hartley, D. F. *J. Nucl. Med.* 1996 37(8):1380–1384). Several groups have attempted to use SA and biotinylated antibodies for in vivo applications such as gamma-immunoscintography (Hnatowich et al. *J. Nucl. Med.* 1987 28:1294–1302) drug-targeting (Bickel et al. *Proc. Natl. Acad. Sci.* 1993 90:2618–2622; Muzykantov et al. *Am. J. Physiol.* 1996 270:L704–713; Muzykantov et al. *Proc. Natl. Acad. Sci. USA* 1996 93:5213–5218; Muzykantov et al. *J. Pharmacol. Exp. Therap.* 1996 279:1026–1034) and blood clearance (Taylor et al. *Proc. Natl. Acad. Sci. USA* 1991 88:3305–3309; Marshall et al. *Br. J. Cancer* 1994 69:502–507).

When considering antibodies that could be used as potential carriers for effectors, work has focused on the pulmonary endothelium. Binding sites for two particular molecules are found in high concentrations in pulmonary endothelium, platelet endothelial cell adhesion molecule-1, PECAM-1 (Newman, P. J. *J. Clin. Invest.* 1997 99(1):3–7; DeLisser et al. *Trends in Cardiovascular Medicine* 1997 151:671–677) and thrombomodulin, TM (Kennel et al. *Nucl. Med. Biol.* 1990 17:193–200). Therefore, antibodies to these surface antigens would be excellent candidates for targeting drugs or genetic material to the pulmonary endothelium if they could be effectively delivered intracellularly.

Experiments were performed to determine the effect of biotinylation and conjugation with SA on anti-PECAM binding to immobilized purified PECAM (CD31) and PECAM-expressing cells. The binding characteristics of biotinylated, radiolabeled-anti-PECAM was determined with either direct radioimmunoassay or non-direct ELISA methods, methods well-known to those of skill in the art. The antibodies used included a polyclonal anti-PECAM-1 antibody named "Houston" and three monoclonal antibodies known as mAb62 (an IgG2A that binds to the first IgG like loop), mAb37 (an IgG1 that binds to the same domain), and mAb4G6 (an IgG2b that binds to the sixth-most membrane proximal loop). Antibodies have been biotinylated and designated below as b-Ab or b-mAb. Immobilized PECAM-1 was used in the form of an CD31/Ig-chimera (Sun et al. *J. Biol. Chem.* 1996 271:19561–18570). Four cell systems were tested: human umbilical vein endothelial cells (HUVEC); EAhy926 cells, a PECAM-1 expressing transformed hybrid cell line made by fusing A549 lung cancer cells with HUVEC; REN/PECAM cells, a non-endothelial cell line obtained from REN mesothelioma transformed cells transfected with human or mouse PECAM-1 cDNA; and REN cells, mesothelioma cells that do not express PECAM and served as a negative control cell line.

Results showed that HUVEC cells possess high affinity binding for anti-PECAM with a maximum binding capacity (Bmax) ranging from 1 to $2 \times 10^6$ sites/cell for monoclonal antibodies 37, 4G6 and 62 to 5 to $8 \times 10^6$ sites per cell for "Houston" polyclonal antibody. As a comparison, the Bmax values for anti-ACE and anti-ICAM1 did not exceed $3 \times 10^5$ sites per cell, demonstrating the advantage of PECAM-1 over other potential endothelial targets. The dissociation constant, or Kd of anti-PECAM binding ranged from 5 nM (mAb37) to 200 nM ("Houston"), while mAb62 and mAb4G6 had Kd values in the range of 10 nM, all values indicating high affinity binding. Neither biotinylation generating b-anti-PECAM, nor conjugation with SA altered the affinity of anti-PECAM for binding to immobilized PECAM or to PECAM-expressing cells at 4° C.

The internalization and degradation of anti-PECAM and SA-conjugated b-anti-PECAM was determined using methods previously described by Muzykantov (*Am. J. Physiol.* 1996 270:L704–L713). Although both endothelial cells and non-endothelial cells transfected with PECAM have very high capacity to bind anti-PECAM, these cells demonstrated very limited ability to internalize anti-PECAM. This conclusion is based on the following: first, about 80% of cell-associated $^{125}$I-anti-PECAM could be eluted by acidic buffer, thus indicating that only 20% of anti-PECAM is inaccessible from the medium; second, cellular uptake of $^{125}$I-anti-PECAM at 4° C. was equal to that at 37° C., thus indicating lack of active energy-dependent process of cellular internalization of bound antibody; and third, non-direct fluorescent staining showed that cell-bound anti-PECAM was associated with the plasma membrane, not with intracellular compartments.

The ability of anti-PECAM to undergo internalization following conjugation of biotinylated anti-PECAM antibodies with SA was also examined. Endothelial cells (HUVEC) were incubated for 90 minutes at 37° C. with b-Ab "Houston", b-mAb4G6, or b-mAb62. A significant increase in antibody internalization was induced by streptavidin conjugation for all three antibodies tested; internalization increased from 20% to as much as 90%. SA conjugation, however, did not affect the rate of degradation of the three antibodies. Degradation of b-mAb62/SA complex was only 1% following internalization. Electron microscopy revealed intracellular accumulation of b-mAb 62/SA complex in a large vesicular compartments. Importantly, streptavidin stimulated total uptake of biotinylated anti-PECAM by HUVEC by an order of magnitude (114±5.3 ng/well vs 16.2±0.5 ng/well for non-conjugated b-mAb 62). Streptavidin has no effect on cellular binding and internalization of control b-IgG. Therefore, SA facilitated internalization, allowing these antibodies to enter a cell in higher amounts, without marked degradation in lysosomes.

Importantly, streptavidin provided the same level of enhancement or facilitation of internalization of biotinylated anti-PECAM antibodies, from 20% to 80–90%, in a non-endothelial cell line transfected with PECAM antigen (i.e., REN/PECAM cells). Fluorescent microscopy revealed intracellular accumulation of b-mAb 62/SA in REN/PECAM cells at 37° C., whereas non-conjugated b-mab 62 was associated predominantly with plasma membrane. This result, as well as additional data obtained in REN/PECAM cells and discussed infra, indicate that the method of the present invention is not limited to endothelium, but rather is applicable to a wide variety of the target cells.

The ability of SA to enhance internalization of other antibodies known to be poorly internalizable was also demonstrated. Previous studies have shown that endothelial cells poorly internalize a monoclonal antibody recognizing chondroitin sulphate-dependent epitope of thrombomodulin (Muzykantov et al. *Circulation* 1997 8:43–44). SA significantly increased internalization of this monoclonal antibody against thrombomodulin (anti-TM mAb). In these experiments, anti-TM mAb was biotinylated and conjugated with SA. Control experiments showed that less than 20% of cell-associated radiolabeled anti-TM mAb underwent internalization in cultures of endothelial cells. In contrast, more than 60% of the SA-conjugated biotinylated anti-TM mAb was internalized. SA also stimulated total binding of this antibody. These data indicate that the method of the present invention is not limited to anti-PECAM antibodies, but rather is applicable to a wide variety of poorly internalizable antibodies.

SA conjugation was also shown to stimulate or enhance accumulation of the carrier antibody in a selected target tissue, in this case pulmonary vascular endothelium. Uptake of radiolabeled antibody was tested in three models: perfused rat lungs, intact rats and intact mice. In the first model, isolated rat lung was perfused for one hour with buffer solution containing test antibody. In the intact animal models, rats or mice were sacrificed one hour after intravenous injection of the test antibody in vivo. Anti-PECAM antibody accumulated poorly in the lungs of experimental animals, either by perfusion of the organ or in vivo. In both test systems, anti-PECAM accumulation in lung tissue was in the range of 2–5%. However, when the same biotinylated antibody was conjugated with SA, tissue uptake increased to 40% in perfused rat lung, 30% in intact mice after i.v. injection, and 15% in intact rats after i.v. injection. In fact, the pulmonary targeting and internalization of b-anti-PECAM/SA conjugate exceeded that of anti-ACE, one of the most effective and specific affinity carriers for pulmonary targeting currently known (Table 1).

TABLE 1

|  | anti-ACE | SA/anti-ACE | anti-PECAM | SA/anti-PECAM |
|---|---|---|---|---|
| Binding to HUVEC 37° C. (Bmax) | 1.5–2.5 × $10^5$ | 1.5–2.5 × $10^5$ | 1–5 × $10^6$ | 0.5–2.5 × $10^7$ |
| Internalization | 50% | 60% | 20% | 90% |
| Uptake in Perfused lung | 20% | 20% | 2.5% | 40% |
| Uptake in Rat Lung (in vivo) | 15% | 15% | 2% | 15% |
| Uptake in Mouse Lung (in vivo) | ND | ND | 10% | 30% |

The fact that the effects of SA on b-anti-PECAM internalization occur after intravenous injection and in isolated rat lung preparations, perfused with a blood-free buffer solution, indicates that stimulation of the targeting by SA is mediated by altered interaction of the carrier antibody with the target cell, not by blood or any other systemic activity. Control experiments demonstrated that the effect of SA is specific to anti-PECAM, since control b-IgG conjugated with SA did not bind to cells in culture and did not accumulate in lung tissue.

In a separate series of experiments, performed in anesthetized newborn pigs, alterations in uptake in a regional vasculature by local administration of $^{125}$I-anti-PECAM/SA conjugate via intravascular catheter were examined. Table 2 shows results from these experiments, expressed as % of injected dose accumulated per gram of tissue (Mean±SD or Mean±SEM).

TABLE 2

| Organ | Intravenous | Right Pulmonary Artery | Coronary Artery |
|---|---|---|---|
| Right low lobe, lung | 0.68 ± 0.2 | 1.98 ± 0.15 | 0.66 ± 0.03 |
| Left low lobe, lung | 0.58 ± 0.1 | 0.33 ± 0.04 | 0.64 ± 0.06 |
| Left ventricle, heart | 0.022 ± 0.004 | 0.015 ± 0.004 | 0.075 ± 0.014 |
| Kidney | 0.033 ± 0.004 | 0.018 ± 0.003 | 0.034 ± 0.004 |

Intravenous (i.e. systemic) administration of the conjugate provided homogenous pulmonary uptake, similar in all lobes, with total uptake of approximately 30% of injected conjugate in the lungs (50 grams). Heart and kidney uptake was 20 times lower. Local administration of the conjugate in the right pulmonary artery provided marked elevation of the uptake in the right lung lobes (e.g. from 0.7 to 2% ID/g in the low lobe). In contrast, uptake in the left lobes and extrapulmonary tissues was reduced two-fold, most likely due to depletion of the conjugate during the first passage through extended lung vasculature. Importantly, intracoronary administration of the conjugate provided a three-fold increase of the targeting to the left ventricle, whereas uptake in the lungs and extrapulmonary tissues (e.g. kidney) remained unchanged compared with intravenous administration. Thus, since a marked reduction after coronary administration was not observed, pulmonary targeting of anti-PECAM/SA can not be the result of mechanical embolization of the pulmonary capillaries by the conjugate. Further, local administration of the conjugate via a catheter offers site-selective targeting of tissues. This is particularly useful when the selected tissue is endothelium localized to coronary, renal or tumor blood vessels.

The method of the present invention, enhancement of internalization and targeting of antibodies, and in particular poorly internalizable antibodies with an average internalization of less than 20%, has potential applications for intracellular delivery of a variety of effectors. Effectors include, but are not limited to, immunotoxins, drugs, enzymes, antisense oligonucleotides, RNA and DNA. The ability of this method to avoid lysosomal degradation is especially important.

The ability of the method of the present invention to deliver an effector to a target cell and enhance internalization of that effector by the cell was examined using a biotinylated hydrogen peroxide-generating enzyme, glucose oxidase (GOX). GOX was conjugated with biotinylated anti-PECAM using SA as a crosslinker, according to the protocol developed in our lab and utilized for conjugation of b-catalase in experiments described below (Muzykantov, V. R. Biotech. Appl. Biochem. 1997 26:103–109). Results showed that anti-PECAM/GOX bound to PECAM/CD31-coated wells, but not to albumin-coated wells, and generated hydrogen peroxide in the CD31-coated wells thus demonstrating the antigen-binding and enzymatic activity of the conjugate. Further, anti-PECAM/radiolabeled-GOX specifically bound to HUVEC and REN-PECAM cells (i.e., PECAM-expressing cells), but not to control REN cells, demonstrating the specificity of the interaction of the antibody conjugate. Using glycine elution techniques, experiments showed that more than 69% of cell-associated anti-PECAM/GOX conjugate was internalized. Experiments also showed that anti-PECAM/GOX conjugates that bound to REN-PECAM cells were able to generate hydrogen peroxide once inside the cells (using fluorescent dye techniques) and then killed the target cells, as measured by $^{51}$chromium release. Cellular fluorescence did not change in the presence of extracellular catalase, an enzyme that degrades hydrogen peroxide, indicating that hydrogen peroxide generated by the cell-associated anti-PECAM/SA/GOX is inaccessible from the extracellular medium and confirming that an active GOX had been delivered internally. Control IgG/GOX conjugates did not bind to antigen or target cells and produced no physiological effects. Fluorescence in the cell lysates was quantitated in a spectrofluorimeter. Results showed that 90% of the fluorescence detected in anti-PECAM/SA/GOX-treated cells was localized intracellularly, while in IgG/GOX cells, 90% of fluorescence was located in the cellular medium. These data confirm the ability of the method of the present invention to provide intracellular delivery of an effector that has biological activity intracellularly.

Experiments were also performed using the conjugated hydrogen peroxide-degrading enzyme, catalase. The enzyme was conjugated to the same carrier antibody using the SA-crosslinker (Muzykantov, V. R. Biotech. Appl. Biochem. 1997 26:103–109). Antibody-conjugated catalase bound to the antigen and the antigen-expressing cells. Tracing the radiolabelled catalase showed that 91% of anti-PECAM/SA/catalase was internalized, while only 4.4% of the internalized material was degraded. Therefore, the method of the present invention allowed for intracellular delivery of a large amount of a therapeutic enzyme, more than 50 ng/well versus 1 ng/well for non-conjugated catalase or IgG/SA/catalase. As before, intracellularly delivered anti-PECAM/SA/catalase was biologically active, as shown by its ability to degrade hydrogen peroxide and protect the cells against oxidative injury induced by the hydrogen peroxide.

A radiolabelled DNA plasmid has also been conjugated to anti-PECAM using the SA crosslinker. Anti-PECAM/SA/$^{31}$P-DNA was shown to specifically bind to the antigen-coated plastic wells and to antigen-expressing cells, HUVEC and REN/PECAM. Approximately 90% of cell-associated anti-PECAM/SA/DNA underwent internalization. Neither DNA by itself nor IgG/SA/DNA conjugate bound to or entered the cells. The DNA encoded fluorescent green protein and when conjugated with the carrier was able to internalize and lead to synthesis of fluorescent green protein in those cells. Neither IgG/SA/DNA conjugate nor DNA mixed with antibody caused transfection of the target cells, demonstrating that the SA-mediated conjugation of DNA to the carrier antibody, anti-PECAM, was necessary for transfection of the cells.

TABLE 3

|  | REN/PECAM cells | REN cells |
|---|---|---|
| Lipofectin-DNA | 240 ± 10 | 250 ± 11 |
| Anti-PECAM/SA/DNA | 145 ± 5 | 11 ± 5 |
| IgG/SA/DNA | 10 ± 4 | 11 ± 3 |

Data are shown in Table 3 as number of fluorescent cells per well, Mean±S.D., n=3. Cells transfected with DNA encoding fluorescent green protein synthesize this protein and render green fluorescence. In a control experiment, lipofectin provided relatively more effective, but non-specific (in terms of targeting to the specific antigen, PECAM) transfection of either REN cells or REN cells expressing PECAM. In contrast, DNA conjugated with anti-PECAM/SA carrier provided transfection of PECAM-positive, but not control REN cells. Transfection is clearly mediated by anti-PECAM/SA carrier, since IgG/SA carrier provided no significant transfection of either REN or REN/PECAM cells.

Several in vivo experiments were performed to confirm that an enzyme delivered to the pulmonary endothelium is active and capable of producing a local effect. Two in vivo models were used, isolated rat lungs and intact mice.

To test the ability of anti-PECAM/SA to deliver an active drug to the pulmonary endothelium, b-anti-PECAM/SA/b-$^{125}$I-catalase or b-IgG/SA/b-$^{125}$I-catalase were injected intravenously into intact animals. In rats, b-mab 62/SA/b-$^{125}$I-catalase specifically accumulated in rat lungs after intravenous injection, with lung/blood ratio in rats 39.8±4.1 for b-mAb 62/SA/b-$^{125}$I-catalase versus 1.1±0.2 for b-IgG/SA/b-$^{125}$I-catalase. Similar results were seen in mice, with lung/blood ratios equal to 7.5±1.1 for b-mAb 390/SA/b-$^{125}$I-catalase versus 0.6±0.1 for b-IgG/SA/b-$^{125}$I-catalase. Therefore, anti-PECAM/SA, but not IgG/SA, delivers catalase to the pulmonary vasculature after intravenous administration in intact animals.

The ability of b-mAb 62/SA/b-catalase to protect the lung against intravascular oxidative insult in the perfused rat lungs was examined. In the first experiment, the uptake of b-mAb 62/SA/b-$^{125}$I-catalase and b-IgG/SA/b-$^{125}$I-catalase in isolated perfused lungs was determined to be 37.3±4.4% versus 2.1±0.2% ID/g (1 hour perfusion). In the second experiment, perfusion of 5 mM $H_2O_2$ was performed in isolated perfused rat lungs. This intervention causes lung injury resulting in elevation of the lung wet-to-dry ratio which reflects lung edema. Isolated rat lungs were first perfused for 1 hour with 100 μg of either b-mAb 62/SA/b-catalase, b-IgG/SA/b-catalase or buffer alone. After elimination of non-bound material, lungs were further perfused with 5 mM $H_2O_2$ for 60 minutes. In perfused lungs treated with b-IgG/SA/b-catalase, the wet-to-dry weight ratio (8.1±0.7) was markedly higher (p<0.001) than that in the control lungs not treated with $H_2O_2$ (5.1±0.2), thus indicating lack of protection against $H_2O_2$. In contrast, in isolated perfused lungs treated with b-mab 62/SA/b-catalase, the wet-to-dry weight ratio remained normal (5.5±0.1), thus indicating protection of the lung against $H_2O_2$-induced oxidative vascular injury.

For the perfused lung experiments, an isolated organ in vivo model, lungs were perfused with either 100 μg anti-PECAM/SA/GOX or 100 μg of IgG/GOX. Before addition of the conjugate to the perfusate, lungs were perfused with a fluorescent probe, H2DCFda. In this reaction, generation of hydrogen peroxide in the lung leads to conversion of H2DCFda to a fluorescent dye, DCF. Results showed that DCF fluorescence in the lungs perfused with anti-PECAM/SA/GOX was several times higher (approximately a 5-fold increase) than that in lungs perfused with IgG/GOX. This result indicates that GOX had accumulated in lung tissue and retained its functional activity, generation of hydrogen peroxide. The effect of generation of hydrogen peroxide in lung was then examined by determining the activity of ACE, where elevation of ACE activity is indicative of endothelial injury. Studies have shown this endpoint to be a sensitive and cell-specific marker of oxidative endothelial stress in the lung (Atochina et al. *AJRCCM* 1997 156:1114–1119). Activity of ACE was increased significantly, approximately 3-fold, with perfusion of anti-PECAM/SA/GOX.

Pulmonary uptake of anti-PECAM/$^{125}$-GOX in the isolated rat lungs attained 20% injected dose/gram (ID/g), while that of IgG/$^{125}$I-GOX did not exceed 0.5% ID/g. One hour after intravenous injection in intact BALB/c mice, the blood level of anti-PECAM/$^{125}$I-GOX was similar to that of IgG/$^{125}$I-GOX (2.9±0.2 versus 2.7±0.1% ID/g. In contrast, pulmonary uptake of anti-PECAM/$^{125}$I-GOX achieved 30% ID/g and was ten times higher than that of IgG/$^{125}$I-GOX. The lung/blood ratio was 10.6±1.6 for anti-PECAM/$^{125}$I-GOX versus 0.9±0.1 for IgG/$^{125}$I-GOX. Therefore, anti-PECAM/SA, but not IgG/SA, delivers glucose oxidase to the pulmonary vasculature either in the isolated animal lungs or after intravenous administration in intact animals.

The functional effects of anti-PECAM/SA/GOX were also tested in intact mice, a whole animal in vivo model. Mice were injected intravenously with either anti-PECAM/SA/GOX or IgG/GOX or anti-PECAM (100 μg of each conjugate). The goal was to evaluate whether tissue-specific intracellular accumulation of GOX would lead to detectable manifestations of GOX activity in lung tissue. High lethality was seen in the first several hours after injection of 100 μg of anti-PECAM/SA/GOX, with more than 80% of animals dying due to treatment with this antibody-enzyme conjugate. In contrast, neither IgG/GOX or anti-PECAM caused significant lethality; only one death was reported in either of these groups and was attributed to anesthesia overdose. The induction of lethality was dose-dependent, occurring at doses of anti-PECAM/SA/GOX exceeding 50 μg (dose range of 0, 25, 50 and 100 μg). The results showed that lethality increased from 0% at doses of 25 μg anti-PECAM/SA/GOX, to approximately 70% at 50 μg anti-PECAM/SA/GOX, to more than 80% at the highest dose (100 μg anti-PECAM/SA/GOX). In addition, injection of the anti-PECAM/SA/GOX conjugate led to a significant increase in lung wet/dry ratio, indicative of an elevation of pulmonary vascular permeability and lung injury; the ratio increased from less than 5 with control treatments (PBS, antibody alone, or IgG/GOX) to more than 7 in animals administered anti-PECAM/SA/GOX. Morphological examination revealed that anti-PECAM/SA/GOX induced specific and local injury to the lung, with no injury seen in heart, liver or spleen. Electron microscopy showed that pulmonary endothelium was the site of the injury.

Each of these experiments with conjugated enzymes (GOX and catalase) and conjugated DNA demonstrates that the method of the present invention provides specific recognition of antigen-expressing target cells, internalization of the conjugate, escape from intracellular degradation, and a functional conjugate capable of producing specific physiological effects intracellularly. The method also has been shown to be capable of specifically targeting pulmonary vascular endothelium after systemic administration in vivo. Further, experiments in intact mice administered conjugated GOX indicate the method of the present invention would be useful for targeting selected cells and killing such cells. One embodiment of this would be targeting tumor cells in a tissue with an antibody carrier targeted to the particular tumor and conjugated with an enzyme that produces cell death, such as GOX.

The conjugated effectors can be selected from, but are not limited to, a wide variety of drug classes that include immunotoxins, antisense oligonucleotides, nucleic acids, intracellular hormones, and antioxidants. One of skill would be able to determine which effector to conjugate with the biotinylated-SA-antibody. One of skill would be familiar with methods to formulate the conjugated antibody for administration to an animal. An animal in this case would be any human or non-human species. The conjugated antibody-effector compounds could be administered either systemically (i.e., intravenously, intramuscularly, subcutaneously, by inhalation) or locally to the site of desired action. Administration would be in any pharmaceutically acceptable carrier, including but not limited to saline, carboxymethylcellulose, or other polyethylene glycol-derived vehicles. One of skill in the art would be able to choose the appropriate vehicle and then determine dosage based on their training and knowledge of the disease or condition to be treated and their knowledge concerning the effector chosen for administration.

The following non-limiting examples are presented to further illustrate the claimed invention.

EXAMPLES

Example 1

Biotinylation, Radiolabeling of Proteins Preparation of the Conjugates and Assessment of Activity Biotin ester, 6-biotinylaminocaproic acid N-hydroxysuccinimide ester (BxNHS) was dissolved in 100% dimethylformamide to a final concentration of 10 mM or 1 mM. Control mouse IgG, anti-ACE mAb 9B9, anti-PECAM-1 mAb 62, mAb 4G6, mAb 37, mAb 390, and polyclonal antibody "Houston" were biotinylated at ten-fold molar excess of BxNHS. Eight μl of fresh 1 mM BxNHS were added to 100 μl of antibody colution (1 mg/ml in borate buffered saline, BBS, pH 8.1). After a 1 hour incubation on ice, excess non-reacted BxNHS was eliminated by overnight dialysis. Catalase was biotinylated by the same reagent at 15-fold molar excess of BxNHS, as described above. Biotinylated glucose oxidase was from Sigma (b-GOX). Biotinylated antibodies, b-GOX and b-catalase were radiolabeled with $^{125}$iodine using Iodogen-coated tubes according to the manufacturer's recommendations (Pierce), by the conventional procedure described by Hiemish et al. *Nucl. Med. Biol.* 1993 20:435–444. Incubation of 100 μg of a biotinylated protein and 100 μCi of sodium $^{125}$iodide in a tube coated with 100 µg of Iodogen for 20 minutes on ice yields streptavidin with a specific radioactivity of approximately 500 cpm per ng. Excess iodine was eliminated by dialysis. More than 95% of radiolabeled proteins were precipitable by TCA.

Tri-molecular heteropolymer complexes, b-catalase/SA/b-IgG or b-catalase/SA/b-anti-PECAM, were prepared by a two-step procedure. Specifically, at the first step, streptavidin (SA) and b-catalase were mixed at molar ratio SA:b-catalase equal 5, in order to form bi-molecular complexes b-catalase/SA. Accordingly, 10 µl of BBS containing 10 µg of radiolabeled b-catalase was mixed with 10 µl of BBS containing 15 µg of streptavidin and incubated for 1 hour on ice. The mixture was then divided by two portions, 10 µl each. To the first portion was added 15 µl of BBS containing 15 µg of biotinylated anti-PECAM. To the second portion was added 15 µl of BBS containing 15 µg of control IgG. These mixtures were then incubated for two hours on ice, in order to form tri-molecular conjugates b-catalase/SA/b-anti-PECAM or b-catalase/SA/b-IgG. The same procedure has been utilized to generate tri-molecular complexes b-GOX/SA/b-IgG, b-GOX/SA/b-anti-PECAM, DNA/polylysin/SA/b-anti-PECAM and DNA/polylysin-SA/b-IgG.

Catalase activity was determined by the rate of hydrogen peroxide decomposition. Ten microliters of BBS-BSA containing 0.1 or 1 µg of catalase, b-catalase or b-antibody/SA/b-catalase conjugate were added to a cuvette containing 3 ml of 10 mM solution of $H_2O_2$. Optical density in the cuvette was measured at 234 nm before addition of catalase and each 30 seconds during the first three minutes after catalase addition. To determine $H_2O_2$ concentration in the cuvette, a calibration curve of $H_2O_2$ optical density at 234 nm was plotted in the concentration range 0.5–10 mM. Catalase activity was calculated as units per mg of protein (1 unit decomposes 1 µM of $H_2O_2$ per minute).

To determine antigen-binding capacity of anti-PECAM, anti-PECAM/SA or anti-PECAM/SA/b-enzymes, 96-well microtest plates coated with an antigen, PECAM-1 (CD31) were used. For immobilization, 100 µl of BBS (pH 8.1) containing 100 ng of PECAM-1 was incubated overnight in the wells at 4° C. The wells were then washed, blocked with BBS buffer containing 2 mg/ml of bovine serum albumin, BSA (BBS-BSA) for 1 hour at room temperature to block sites for non-specific binding. One hundred microliters of BBS-BSA containing 10, 30, 100, 300 or 1,000 ng of biotinylated $^{125}$I-antibodies or the conjugates was incubated in wells for 1 hour. After washing, radioactivity in the wells was measured.

Example 2

Interaction of Radiolabeled Antibodies with Cultured Human Endothelial Cells

Binding, internalization and cellular degradation of radiolabeled anti-PECAM, b-anti-PECAM/SA or enzymes and DNA conjugated with b-anti-PECAM/SA, were determined. Specifically, cultivated cells (HUVEC, REN/PECAM or control REN cells) were cultured in gelatin-coated plastic dishes ("Falcon") using Medium 199 with Earle's salts supplemented with 10% fetal calf serum, 200 µg/ml endothelial growth factor from human brain and 100 µg/ml heparin, 2 mM glutamine, 100 mU/ml penicillin and 100 µg/ml streptomycin. Cells were subcultivated from first to third passage by treatment with 0.05% trypsin/0.02% EDTA mixture.

For binding experiments, cells were subcultured in 96-well microtiter plates for 5 days to reach confluence. For estimation of cellular binding, 10–10,000 ng of $^{125}$I-antibody or control $^{125}$I-IgG was added to washed cells in 300 µl of M199 culture medium containing 0.2% BSA and incubated for 60 minutes at 4° C. or 37° C. After washing with M199, cells were detached using standard trypsin/EDTA mixture and cell-associated radioactivity was estimated in a gamma-counter.

To determine the internalization of antibodies by the endothelium, cells were incubated with 300 µl of culture medium containing 1 µg $^{125}$I-b-anti-PECAM or $^{125}$I-b-anti-PECAM/SA for 90 minutes at 37° C. After washing to remove unbound radioactivity, cells were incubated with 50 mM glycine, 100 mM NaCl, pH 2.5 (15 minutes at room temperature) to release surface associated antibody. There was no detectable cell detachment after treatment with glycine buffer as determined by light microscopy. After collection of the glycine eluates, cells were detached by incubation with standard trypsin/EDTA solution. Surface associated radioactivity (i.e., radioactivity of the glycine eluates) and cell associated radioactivity (i.e., radioactivity of trypsin/EDTA extracts) were determined in a gamma counter. Percent of internalization was calculated as %=(total radioactivity−glycine eluted)×100/total radioactivity.

To determine degradation of the antibody and detachment of radiolabel from the antibody molecule a standard assay of TCA soluble radiolabel was used. Specifically, 200 µl of 100% TCA was added to 1 ml of a sample of the cellular lysate. After a 1 hour incubation at 4° C., samples were centrifuged at 2,000 rpm for 10 minutes and radioactivity in the pellet and supernatants was determined. The percentage of TCA soluble radiolabel (i.e., percent of degradation) was calculated as %=(radioactivity of supernatant)×100/total radioactivity.

Example 3

Perfusion of the Isolated Rat Lung

Sprague-Dawley male rats, weighing 170–200 g, were anesthetized with sodium pentobarbital, 50 mg/kg, i.p., and prepared for isolated lung perfusion using recirculating perfusate as previously described by Muzykantov et al. *Am. J. Physiol.* 1996 270:L704–713. The trachea was cannulated and lungs were ventilated with a humidified gas mixture (Airco Inc., Philadelphia, Pa.) containing 5% $CO_2$ and 95% air. Ventilation was performed using a SAR-830 rodent ventilator (CWE Inc., Ardmore, Pa.) at 60 cycles/minute, 2 ml tidal volume, and 2 cm $H_2O$ end-expiratory pressure. The thorax was then opened and a cannula was placed in the main pulmonary artery through the transected heart. The lungs were isolated from the thorax and initially perfused in a non-recirculating manner for a 5 minute equilibration period, in order to eliminate blood from the pulmonary vascular bed. The lungs were then transferred to the water-jacketed perfusion chamber maintained at 37° C. Perfusion through the pulmonary artery was maintained by a peristaltic pump at a constant flow rate of 10 ml/minute. The perfusate (45 ml per lung) was Krebs-Ringer buffer (pH 7.4), containing 10 mM glucose and 3% fatty acid-free BSA. Perfusate was filtered through a 0.4 µm filter prior to perfusion to eliminate particulates. Intratracheal and pulmonary arterial pressures were continuously recorded throughout the experiment with pressure transducers PM 131TC and P23DC (Statham Instruments, Oxnard, Calif.), direct writing oscillographs (Gould, Cleveland, Ohio) and AC recorders (Primeline, Sun Valley, Calif.). Zero reference for perfusion pressure was determined at the end of each experiment and was defined as a pressure measured at the experimental flow rate without the lungs being connected to the circuit.

Following isolation of the lungs, the lungs were initially perfused with KRB-BSA solution for a 5 minute equilibration period. One microgram of $^{125}$I-antibodies or antibody-conjugated compounds was then added to the perfusate. After a one hour perfusion, lungs were perfused in a non-recirculating manner for 5 minutes with KRB-BSA solution to eliminate non-bound radiolabeled albumin. A similar protocol was utilized to determine the pulmonary uptake of radiolabeled antibodies conjugated with streptavidin, as well as radiolabeled catalase or GOX conjugated with antibodies. After elimination of non-bound radiolabeled material, lungs were removed from the chamber, rinsed with saline, blotted with a filter paper, and the extraneous cardiac and bronchial structures were dissected away. The left lobe was removed, blotted with a filter paper, its wet weight was determined and its radioactivity was measured in a gamma-counter and expressed as a percentage of perfused radioactivity per gram of the lung tissue (% ID/g).

ACE activity in the perfusates, serving a parameter of endothelial oxidative injury by GOX/SA/anti-PECAM, was measured by the rate of generation of His-Leu formed from the ACE substrate Z-Phe-His-Leu using a fluorometric assay. Ten microliters of the perfusate was added to 200 µl of 50 mM Tris-HCl, 0.15 M NaCl, pH 8.3 buffer, containing 0.5 mM substrate. Samples of perfusate were incubated at 37° C. for 120 minutes. The reaction was terminated by the addition of 1.5 ml of 0.28 N NaOH. O-phthalaldehyde (1 mg in 100 µl methanol) was added for 10 minutes before stopping this reaction with 200 µl 2 N HCl. His-Leu was measured with a fluorescence spectrophotometer at an excitation wavelength of 363 nm and an emission wavelength of 500 nm. Results were calculated as milliunits (mU) of ACE activity per total perfusate (45 ml), where 1 mU represents the generation of 1 nmole His-Leu/minute.

Example 4

Biodistribution of Radiolabeled Antibodies or Antibody-Conjugated Compounds in Animals To study biodistribution of radiolabeled preparations in rats or mice, injection of 0.5 ml of saline containing 1 µg of radiolabeled anti-PECAM or b-anti-PECAM conjugate was made into the tail vein under anesthesia. Control animals were injected with radiolabeled IgG or complexes containing b-IgG instead of b-anti-PECAM. Animals were sacrificed by exsanguination 60 minutes after injection. Radioactivity in the blood and tissues was determined as described by Muzykantov et al. *Proc. Natl. Acad. Sci. USA* 1996 93:5213–5218. Internal organs were washed with saline to remove blood and radioactivity in tissues was determined in a Rack-Gamma counter. The data were calculated as mean±standard error (M±SE). Statistical comparisons were made using one-way analysis of equal variance (ANOVA) followed by Student-Newman-Keuls Method. The level of statistical significance was taken as $p<0.05$.

What is claimed is:

1. A method of increasing cellular internalization or accumulation of a poorly internalized antibody in a target cell, said method comprising:
    (a) biotinylating a poorly internalized antibody recognizing a specific antigen on a surface of a target cell, said poorly internalized antibody exhibiting cellular internalization of less than 20% in the target cell; and
    (b) conjugating the biotinylated antibody of step (a) with streptavidin to produce a streptavidin-biotinylated antibody conjugate, wherein cellular internalization or accumulation of said streptavidin-biotinylated antibody conjugate in the target cell is increased as compared to cellular internalization or accumulation of said poorly internalized antibody.

2. A method for intracellularly delivering an effector to a target cell of an animal comprising:
    (a) biotinylating a poorly internalized antibody recognizing a specific antigen on a surface of a target cell, said poorly internalized antibody exhibiting cellular internalization of less than 20% in the target cell;
    (b) conjugating the biotinylated antibody with streptavidin to form a streptavidin-biotinylated antibody carrier;
    (c) conjugating said streptavidin-biotinylated antibody carrier with an effector; and
    (d) administering the streptavidin-biotinylated antibody carrier-effector conjugate to an animal so that the effector of the conjugate formed in step (c) is delivered intracellularly to the target cell.

3. The method of claim 2 wherein the effector produces oxidative injury in the target cells when delivered intracellularly thereby killing the target cells.

* * * * *